United States Patent [19]

Hutson, Jr. et al.

[11] 4,429,173
[45] Jan. 31, 1984

[54] PRODUCTION OF HIGH-OCTANE, UNLEADED MOTOR FUEL BY ALKYLATION OF ISOBUTANE WITH ISOAMYLENES OBTAINED BY DEHYDROGENATION OF ISOPENTANE

[75] Inventors: Thomas Hutson, Jr.; Paul D. Hann, both of Bartlesville, Okla.

[73] Assignee: Phillips Petroleum Company, Bartlesville, Okla.

[21] Appl. No.: 356,592

[22] Filed: Mar. 9, 1982

[51] Int. Cl.³ .................................................. C07C 3/54
[52] U.S. Cl. .................................. 585/331; 585/314; 585/315; 585/316; 585/332; 585/716; 585/717; 585/719; 585/723
[58] Field of Search ............... 585/314, 315, 316, 331, 585/715, 716, 717, 719, 722, 726, 727, 332, 723

[56] References Cited

U.S. PATENT DOCUMENTS

| | | | |
|---|---|---|---|
| 2,450,038 | 9/1948 | Frey | 585/671 |
| 3,530,060 | 9/1970 | Offenhauer | 585/331 |
| 3,660,520 | 5/1972 | Hemminger | 585/331 |
| 3,686,354 | 8/1972 | Herbert | 585/331 |
| 3,778,489 | 12/1973 | Parker et al. | 585/722 |
| 3,855,344 | 12/1974 | Jones | 585/717 |

*Primary Examiner*—Delbert E. Gantz
*Assistant Examiner*—A. Pal

[57] ABSTRACT

A process combination, with inter-cooperation, for producing high-octane alkylates comprising
(a) dehydrogenating isopentane to isopentenes (amylenes),
(b) introducing the mixture of said amylenes and unconverted isopentane into an HF alkylation unit for reaction with fresh or recycled isobutane,
(c) separating the alkylation products into high octane alkylates, isopentane (for recycling to the dehydrogenation reactor) and isobutane (for recycling to the alkylation reactor).

12 Claims, 1 Drawing Figure

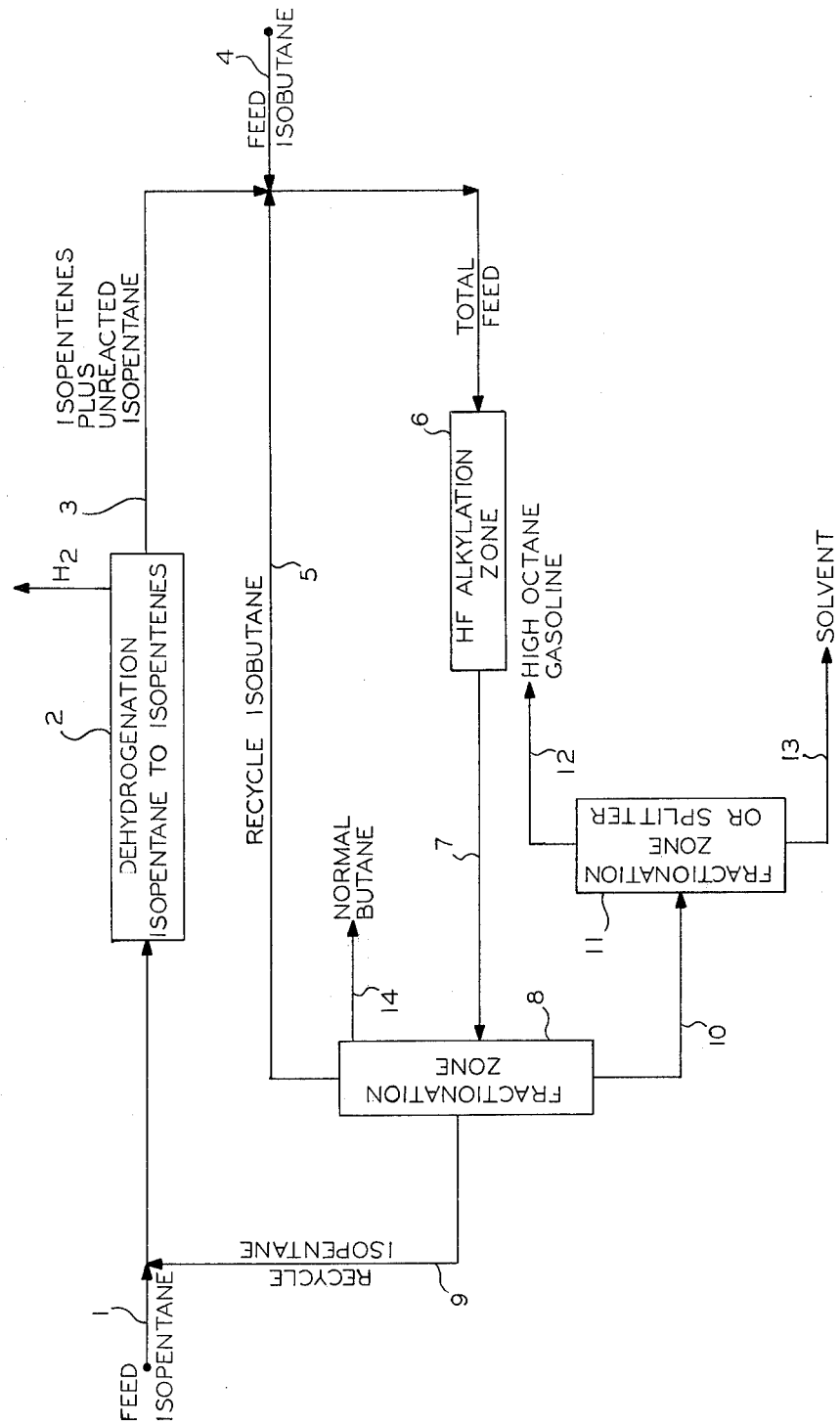

PRODUCTION OF HIGH-OCTANE, UNLEADED MOTOR FUEL BY ALKYLATION OF ISOBUTANE WITH ISOAMYLENES OBTAINED BY DEHYDROGENATION OF ISOPENTANE

This invention relates to alkylation of hydrocarbons. In another aspect, this invention relates to processes for treating organic compounds with hydrogen fluoride (HF). In another aspect, this invention relates to a combination process for the production of alkylate motor fuel. In another aspect, this invention relates to an improved process for the production of a superoctane HF alkylate motor fuel by the HF alkylation of isobutane with isoamylenes which are obtained by dehydrogenation of isopentane. In another aspect, this invention relates to the improvement of said HF alkylate motor fuel by the separation therefrom of isobutane and isopentane, which are recycled to HF alkylation zone feed and a dehydrogenation step, respectively.

SUMMARY OF THE INVENTION

This invention is a combination process for production of superoctane HF alkylate by HF alkylation of isobutane with isoamylenes, requiring two hydrocarbon feed streams (isobutane and isopentane), in which the HF alkylate is improved by the separation of unreacted isobutane and isopentane, which are recycled to HF alkylation zone feed and a dehydrogenation step, respectively.

It is an object of this invention to prepare a gasoline of low volatility having a high octane number. It is another object of this invention to prepare said gasoline by a process comprising the steps of dehydrogenating isopentanes to isopentenes (isoamylenes) and alkylating isobutane with these isoamylenes. Other objects, aspects, as well as the several advantages of the invention will be clear to one skilled in the art upon a study of the disclosure, including the description of the drawing and the appended claims.

The dehydrogenation of isopentane is well known and is disclosed in a number of U.S. Patents, e.g. U.S. Pat. Nos. 3,737,473 and 3,291,855. The HF catalyzed alkylation of isobutane with isopentenes is known in principle and is disclosed in various U.S. Patents, e.g. U.S. Pat. Nos. 2,375,867 and 4,144,281. This invention is a combination of these two known processes that produces a gasoline of unexpectedly high octane number and low volatility.

There is increasing pressure on the refining industry to produce unleaded high octane motor fuels to meet federally-mandated requirements for new automobile fleets. (See, e.g., U.S. Pat. No. 3,787,313.) Most newly-manufactured cars are required to use unleaded fuels, and the gradual increase in octane number requirement as such cars accumulate mileage has led to increasing demand for unleaded gasolines of high octane ratings. The problems of producing such fuels are aggravated by the relative scarcity of desirable crude oils. This invention makes significant contribution to the attainment of these federally mandated goals by converting an isoparaffin (isopentane) with a research octane number (RON) of only 93 to a motor fuel having a RON of about 101. In addition, this conversion results in a reduction of the Reid vapor pressure (RVP) from 15 psi for isopentane to about 1-2 psi for the alkylate, which is therefore less prone to cause air pollution, fuel waste and vapor-lock in automobile engines.

It is to be emphasized that even though the alkylation of isobutane with isoamylenes (isopentenes) is known in principle, it is not generally practical because it produces a large amount of volatile paraffins (iso-and n-pentane) by hydrogen transfer side reactions, thus resulting in an undesirably high vapor pressure of the alkylate. These undesirable side reactions occur only to an insignificant extent in the alkylation of isobutane with butylenes and propylene. Therefore, these alkylation processes have hitherto been preferred to alkylation with isoamylenes.

This invention results in an unexpected improvement over the separate dehydrogenation of isopentane and alkylation of isobutane with isopentenes in that the inventive combination process does not produce such highly volatile compounds and in that it can commercially compete with the widely practiced isobutane alkylation with butylene and/or propylene.

In the HF alkylation of isobutane with olefins, the produced isopentane is recovered in the motor fuel alkylate. Since isopentane has a relatively high vapor pressure (20.3 psi at 100° F.), and since motor fuel is blended for seasonal use at about 7 psia vapor pressure at 100° F. in the summer and about 14 psia vapor pressure at 100° F. in the winter, the amount of isopentane which can be used in the motor fuel is limited because of its high vapor pressure. Also, the Research Octane Number without added tetra-ethyl lead ("lead" free) is only about 93.

This invention utilizes isopentane from an outside source plus isopentane produced in the HF alkylation of isobutane to produce isoamylenes, which are then used to HF alkylate isobutane.

By operating in the manner of our invention, we minimize the amount of isopentane in the motor fuel alkylate and utilize this isopentane to produce isoamylenes, which when used to HF alkylate isobutane, produces our superoctane alkylate. Each mol of isopentane (as isoamylenes) reacts with a mol of isobutane to yield a mol of superoctane alkylate. We thus use one volume of isopentane (via conversion into isoamylenes to HF alkylate isobutane) and produce about 1.8 volumes of superoctane HF alkylate from this one volume of isopentane. We thus increase the volume of gasoline produced per mol of isopentane (and gasoline is sold by volume) and also increase the octane rating of this gasoline by using isopentane (both from an outside source and that produced during alkylation) as set out in our invention.

This invention is a combination process for the production of a superoctane alkylate motor fuel by the HF alkylation of isobutane with isoamylenes. The alkylation unit uses a conventional liquid HF catalyst. The alkylate is passed through a fractionation zone, where unreacted isobutane and isopentane are removed. The recovered isobutane is recycled to the alkylation zone, while recovered isopentane is recycled to the same dehydrogenation zone which is used to produce isoamylenes (for the HF alkylation step) from feed isopentane.

BRIEF DESCRIPTION OF THE DRAWING

The sole FIGURE is a schematic flow diagram illustrating a specific embodiment of the invention as applied to a combination process for production of HF alkylate motor fuel. The process of the invention will now be described with reference to the drawing. It is to be understood that numerous items of equipment, such as pumps, valves, and the like, have been omitted from the drawing so as to simplify the description of the invention. Those skilled in the art will realize that such conventional equipment can be employed as desired.

DETAILED DESCRIPTION OF THE INVENTION

As shown in FIG. 1, the isopentane containing feed stream (1), which can contain some n-pentane, is dehydrogenated in reactor (2) primarily to isopentenes, plus hydrogen as a valuable by-product. Suitable outside sources of isopentane containing some n-pentane can be the light naphtha fraction of an atmospheric crude distillation column or the product of an atmospheric gas oil catalytic cracking process.

The effluent (3) of the dehydrogenation reaction is mixed with isobutane from an outside source (4), plus recycle isobutane (5), and undergoes HF-catalyzed alkylation in reactor (6). The alkylate (7) is separated in a first fractionation zone (8) into three product streams: recycle isobutane (5); recycle isopentane (9) containing some n-pentane and being combined with isopentane feed (1); a gasoline product (10) containing all hydrocarbons with 6 or more carbon atoms. The gasoline fraction (10) can optionally be fractionated in a second fractionation zone or splitter (11) into a high RON gasoline fraction (12) containing isohexanes, isoheptanes and some isooctanes and a higher boiling fraction (13) containing some isooctanes, isononanes and higher paraffins and having a lower RON than (12). Fraction (13) is suitable as a solvent similar to one marketed under the trademark Soltrol ® by Phillips Petroleum Company. Such solvents are semi-odorless, stable, non gum-forming, and useful in paints and the like. A fourth stream (14) is taken from the first fractionation zone to remove normal butane. If the gasoline product has a Reid vapor pressure lower than specified by the government or purchaser, the butane from stream (14), with or without additional butane from an outside source, can be blended into said gasoline up to the point at which said vapor pressure reaches the allowable limit. Much of the butane thus separated through stream (14) can thus be recycled into the gasoline product, maintaining the high octane rating and a tolerable vapor pressure at a reduced cost.

Calculated examples of the process of this invention, carried out in a system as shown in the drawing, are as follows:

EXAMPLE I

In this example the composition and pertinent properties of three alkylation products are compared. Each of the three runs was carried out with isobutane and an olefin at a weight ratio of about 13:1 in a pressurized reactor employing hydrogen fluoride as the catalyst for a time sufficient to convert essentially all olefins to alkylation products, which generally requires about 20–30 seconds.

The volume ratio of liquid HF, containing about 1–2 weight percent of water and 5–7 weight percent of hydrocarbons, to all hydrocarbons (isobutane and olefins) was about 4:1. The pressure was selected so as to keep all reactants and catalyst in the liquid phase, and the reaction temperature was about 95° C.

Three alkylation runs were carried out using isobutane and three different olefins: propylene, butylenes and isoamylenes (isopentenes). The weight percent compositions of the three produced alkylates are given in Table I.

TABLE I

| COMPONENTS | RON[1] OF COMPONENT | OLEFINS USED | | |
|---|---|---|---|---|
| | | RUN 1 PROPYLENE | RUN 2 BUTYLENES | RUN 3 ISOAMYLENES |
| Propane and Butanes | | ~0 wt % | ~0 wt % | ~0 wt % |
| Isopentane | 93.0 | 4.10 | 2.17 | 36.73 |
| Normal Pentane | 61.8 | 0 | 0 | 3.42 |
| 2-Methylpentane | 73.4 | 0.99 | 0.31 | } 1.01 |
| 2,3-Dimethylbutane | 104.3 | 2.31 | 1.14 | |
| 3-Methylpentane | 74.5 | 0.21 | 0.15 | 0.19 |
| 2,2-Dimethylpentane | 91.8 | 0.02 | 0 | } 0.37 |
| 2,4-Dimethylpentane | 83.1 | 14.78 | 1.09 | |
| Triptane | 112.1 | 0 | 0.04 | 0 |
| 2-Methylhexane | 42.4 | 0.20 | 0.05 | 0.02 |
| 2,3-Dimethylpentane | 91.1 | 36.70 | 0.65 | 0.14 |
| 3-Methylhexane | 52.0 | 0.66 | 0.04 | 0.02 |
| 2,2,4-Trimethylpentane | 100.0 | 18.06 | 52.53 | 27.82 |
| 2,5-Dimethylhexane | 55.5 | 0.80 | 2.40 | 0.37 |
| 2,4-Dimethylhexane | 65.2 | 0.83 | 3.41 | 0.22 |
| 2,2,3-Trimethylpentane | 109.6 | 0.30 | 4.32 | 0.11 |
| 2,3,4-Trimethylpentane | 102.7 | 4.60 | 15.63 | 4.58 |
| 2,3,3-Trimethylpentane | 106.1 | 3.07 | 11.41 | 2.54 |
| 2,3-Dimethylhexane | 71.3 | 0.05 | 2.74 | 1.50 |
| 3,4-Dimethylhexane | 76.3 | 0.04 | 0.48 | 0.02 |
| 2,2,5-Trimethylhexane | 91.0 | 0.29 | 0.44 | 10.95 |
| Residue | 80 | 11.95 | 1.00 | 9.99 |
| Molecular Weight | | 107.4 | 113.9 | 96.24 |
| API Gravity 60/60° F.[2] | | 70.3 | 68.7 | 80.2 |
| Reid Vapor Pressure, psi[3] | | 3.79 | 2.36 | 11.66 |
| RON Clear[1] of (A) | | 90.2 | 96.9 | 91.5 |

TABLE 1-continued

| COMPONENTS | RON[1] OF COMPONENT | OLEFINS USED | | |
|---|---|---|---|---|
| | | RUN 1 PROPYLENE | RUN 2 BUTYLENES | RUN 3 ISOAMYLENES |
| RON Clear[1] of (B) | | 91.6 | 98.6 | 95.07 |

(A) Total alkylate;
(B) motor fuel cut (down to and including 2,2,3 trimethylpentane)
[1]Research Octane Number, without lead additive, determined according to ASTM D2699
[2]defined as $\frac{141.5}{\text{Specific Gravity}} - 131.5$, determined at 60° F.
[3]determined according to ASTM D323, at 100° F.

Data in Table I show that the alkylation of isobutane with isoamylenes produces an alkylate containing a considerable amount of pentanes formed by hydrogen transfer side reactions, which are virtually absent in the corresponding alkylation reactions with propylene and butylenes. Pentanes have a much higher vapor pressure than the other alkylation components, thus causing a much higher RVP of the isoamylene alkylate than the RVP of the propylene and butylene alkylates. The research octane number of the isoamylene alkylate is lower than that of the butylene alkylate. This disadvantage prevails even after a fractionation step which separates a higher boiling fraction (2,3-dimethylhexane, 3,4-dimethylhexane, 2,2,5-trimethylhexane, residue; (13 of FIG. 1) of relatively low octane rating from the other, more volatile components. Therefore, the alkylation of isobutane with isoamylenes normally results in two shortcomings versus the most widely practiced alkylation with butylenes: significantly higher vapor pressure and somewhat lower research octane number.

EXAMPLE II

The process of this invention as shown in FIG. 1 would eliminate isopentane and n-pentane from the alkylation product because these compounds would be recycled to the dehydrogenation reactor. This recycling would result in the following product advantages of the amylene alkylate (without the higher boiling fraction containing 2,3- and 3,4-dimethylhexane, 2,2,5-trimethylhexane and residue): an increase in the research octane number (RON) clear from about 95 to about 100.6 and a decrease in Reid vapor pressure (RVP) from about 11.7 psi to about 1.0–2.0 psi. This topped alkylate would compare quite favorably with a corresponding isobutane-butylene alkylate fraction having a RON of about 98.6 and a RVP of about 2.4 psi.

EXAMPLE III

In this example a calculated material balance for the combination process of this invention is presented. 381.1 lb/hr of fresh isopentane feed (1) and 618.9 lb/hr of recycled isopentane (9) (see FIG. 1) are charged to the dehydrogenation reactor (2). The dehydrogenation is carried out at a pressure of about 70 psia, a temperature of about 1050° F., employing a Pt-Sn on zinc aluminate catalyst, while the liquid hourly space velocity (volume of liquid hydrocarbon per volume of catalyst per hour) is about 4.0. About 405 lb/hr of isopentenes, 495 lb/hr of unreacted isopentane, plus 100 lb/hr of hydrogen and various gaseous by-products exit the reactor (2). 900 lb/hr of the liquid dehydrogenation effluent (3) and 531.7 lb/hr of isobutane feed (4) plus 5524.7 lb/hr of recycle isobutane (5) are charged to the alkylation reactor (6) and react under conditions outlined in Example I.

The reactor effluent is fractionated at a pressure of about 125 psia, a top temperature of about 137° F. and a bottom temperature of about 435° F. to yield 787.7 lb/hr of alkylate gasoline (10), 5524.7 lb/hr of recycle isobutane (5), 618.9 lb/hr of recycle isopentane (9), and 25 lb/hr of normal butane yield. Optionally, the gasoline fraction can be separated further in splitter (11) to yield 492.1 lb/hr of a high-octane gasoline (12) and 295.6 lb/hr of a low-octane solvent fraction (13).

Reasonable variations and modifications can be made, or followed, in view of the foregoing disclosure, without departing from the spirit or scope thereof.

We claim:

1. A process for production of high-octane alkylate comprising:
    (a) introducing an isoparaffin selected from the group consisting of isobutane, isopentane, and mixtures thereof, with olefins consisting essentially of amylenes and an HF catalyst into an alkylation reaction zone;
    (b) reacting the materials so introduced into said alkylation reaction zone to form an effluent comprising an alkylate;
    (c) separating said effluent into an HF catalyst phase and a hydrocarbon phase;
    (d) passing said hydrocarbon phase into a first fractionation zone;
    (e) withdrawing said alkylate from said first fractionation zone as a liquid;
    (f) withdrawing a first stream comprising isopentane and a second stream comprising isobutane when present from separate leads or trays of said first fractionation zone;
    (g) recycling at least a portion of said first stream to a dehydrogenation zone in which said portion of said first stream and an isopentane containing feedstream are at least partially dehydrogenated to form the amylenes to be alkylated in said alkylation reaction zone;
    (h) recycling said second stream comprising isobutane when present to a feed conduit to form at least a portion of the isobutane reacted in said alkylation reaction zone; and
    (i) recovering said alkylate as the product of the process.

2. A process in accordance with claim 1, wherein said alkylate is split in a second fractionation zone into a third stream of high octane gasoline and a fourth stream of higher boiling hydrocarbons.

3. A process in accordance with claim 1, wherein said alkylate is a mixture of branched hydrocarbons having at least 6 carbon atoms per molecule, a research octane rating of at least about 91, a Reid vapor pressure of less than about 11 psia, and wherein about 1.8 volumes of alkylate are produced per unit volume of isopentane.

4. A process in accordance with claim 2, wherein said third stream is a high octane gasoline comprising a mixture of branched hydrocarbons having six to eight carbon atoms per molecule, a research octane rating of at least about 100, and a Reid vapor pressure of less than about 2 psia, and wherein said fourth stream is a mixture of branched and normal hydrocarbons having at least eight carbon atoms per molecule suitable as a solvent.

5. A process in accordance with claim 2, wherein a fifth stream is drawn from said first fractionation zone, comprising normal butane.

6. A process in accordance with claims 1, 2, 3 or 4, wherein said alkylate is blended with butane to produce a high octane unleaded gasoline having a Reid vapor pressure less than about 11 psia.

7. A process in accordance with claim 6, wherein said butane comprises butane from the fifth stream of claim 5.

8. A process in accordance with claims 1, 2 or 5, wherein said high octane alkylate is produced without substantial production of more volatile by-products.

9. A method for producing isopentane-free high octane HF alkylate wherein the fresh feed streams are an isobutane feed stream and an isopentane feed stream, and the recycled streams are an isobutane recycle stream and an isopentane recycle stream comprising steps of:
 (a) dehydrogenating at least a portion of said isopentane feed stream and a portion of said isopentane recycle stream to produce isopentenes, yielding an isopentenes-isopentane-containing stream;
 (b) admixing said isopentenes-containing stream from (a) with said isobutane feed stream and said isobutane recycle stream and passing this admixture to an HF alkylation zone wherein at least a portion of the isobutane in said admixture, and at least a portion of the isopentane in said admixture are alkylated in the presence of liquid HF catalyst with the isopentenes in said admixture to produce a hydrocarbon stream comprising unreacted isobutane, unreacted isopentane, and alkylate;
 (c) fractionating said hydrocarbon stream to yield separately said recycle isobutane stream, said recycle isopentane stream, and said isopentane-free high octane HF alkylate.

10. The method according to claim 9 wherein said isopentane-free high octane HF alkylate is further upgraded in octane value by fractionation to remove higher boiling hydrocarbon components.

11. A process in accordance with claim 1 wherein said amylenes are produced by dehydrogenation of said isopentane-containing feed stream.

12. A process for production of high octane alkylate comprising the steps of:
 (a) dehydrogenating a stream comprising isopentane to produce a stream comprising amylenes;
 (b) introducing a stream comprising isobutane and said stream comprising amylenes produced by dehydrogenation of isopentane into a reaction zone with an HF catalyst;
 (c) reacting the materials of (b) so introduced into said reaction zone to form an effluent comprising an HF catalyst, alkylate, isobutane, normal butane, and isopentane;
 (d) separating said effluent into an HF catalyst phase and a hydrocarbon phase;
 (e) recovering isopentane from said hydrocarbon phase;
 (f) recovering normal butane from said hydrocarbon phase;
 (g) recovering isobutane from said hydrocarbon phase;
 (h) recovering said alkylate as a product from said hydrocarbon phase; and
 (i) recycling said isopentane of (e) to said dehydrogenation of (a) as at least a portion of said isopentane of (a).

* * * * *

UNITED STATES PATENT AND TRADEMARK OFFICE
CERTIFICATE OF CORRECTION

PATENT NO. : 4,429,173

DATED : January 31, 1984

INVENTOR(S) : Thomas Hutson, Jr. et al.

It is certified that error appears in the above-identified patent and that said Letters Patent is hereby corrected as shown below:

In claim 9, line 31, after "isopentenes", insert --- -isopentane --.

Signed and Sealed this

Twenty-seventh Day of November 1984

[SEAL]

Attest:

GERALD J. MOSSINGHOFF

Attesting Officer   Commissioner of Patents and Trademarks